United States Patent [19]

Togni et al.

[11] Patent Number: 5,563,309
[45] Date of Patent: *Oct. 8, 1996

[54] FERROCENYL DIPHOSPHINES AS LIGANDS FOR HOMOGENEOUS CATALYSTS

[75] Inventors: Antonio Togni, Oberwil-Lieli; Felix Spindler, Starrkirch-Wil; Nadia Zanetti, Zürich, all of Switzerland; Amina Tijani, Burnhaupt-le-Haut, France

[73] Assignee: Ciba-Geigy Corporation, Tarrytown, N.Y.

[ * ] Notice: The term of this patent shall not extend beyond the expiration date of Pat. No. 5,563,308.

[21] Appl. No.: 459,435

[22] Filed: Jun. 2, 1995

Related U.S. Application Data

[62] Division of Ser. No. 292,150, Aug. 17, 1994, Pat. No. 5,463,097, which is a division of Ser. No. 37,783, Mar. 26, 1993, Pat. No. 5,371,256.

[30] Foreign Application Priority Data

Apr. 2, 1992 [CH] Switzerland .................. 1068/92

[51] Int. Cl.⁶ .................. C07C 5/02; C07F 17/00
[52] U.S. Cl. .................. 585/277; 585/275; 556/14; 556/28; 556/136; 556/146; 526/943
[58] Field of Search .................. 585/275, 277; 556/14, 28, 136, 146

[56] References Cited

U.S. PATENT DOCUMENTS 5,011,995  4/1991  Pugin et al. .................. 564/302

OTHER PUBLICATIONS

T. Hayashi et al., Chem. Soc. of Japan Bull. Chem. Soc. Journal, vol. 53, pp. 1138–1151 (1980).
Tetrahedron Letters No. 14, 1976, pp. 1133–1134, Hayashi.

*Primary Examiner*—Porfirio Nazario-Gonzales
*Attorney, Agent, or Firm*—Kevin T. Mansfield

[57] ABSTRACT

Compounds of formula I

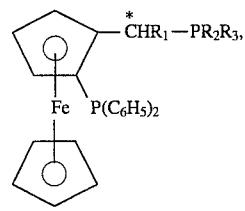

wherein $R_1$ is $C_1$–$C_8$alkyl, phenyl or phenyl which is substituted by 1 to 3 $C_1$–$C_4$alkyl or $C_1$–$C_4$alkoxy groups; $R_2$ and $R_3$ are identical and are $C_1$–$C_{12}$alkyl, $C_5$–$C_{12}$cycloalkyl or $C_1$–$C_4$alkyl- or $C_1$–$C_4$alkoxy-substituted $C_5$–$C_{12}$cycloalkyl, or phenyl which is substituted by one to three identical or different members selected from the group consisting of $C_1$–$C_4$alkyl, $C_1$–$C_4$alkoxy, —$SiR_4R_5R_6$, halogen, —$SO_3M$, —$CO_2M$, —$PO_3M$, —$NR_7R_8$ and —[$^{\oplus}NR_7R_8R_9$]$X^{\ominus}$; or $R_1$ and $R_3$ are different and are $C_1$–$C_{12}$alkyl, $C_5$–$C_{12}$cycloalkyl, $C_1$–$C_4$alkyl- or $C_1$–$C_4$alkoxy-substituted $C_5$–$C_{12}$cycloalkyl, phenyl or phenyl which is substituted by one to three identical or different members selected from the group consisting of $C_1$–$C_4$alkyl, $C_1$–$C_4$alkoxy, —$SiR_4R_5R_6$, halogen, —$SO_3M$, —$CO_2M$, —$PO_3M_2$, —$NR_7R_8$ and —[$^{\oplus}NR_7R_8R_9$]$X^{\ominus}$; or the group —$PR_2R_3$ is a radical of formula II

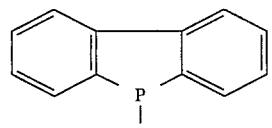

and $R_4$, $R_5$ and $R_6$ are each independently of one another $C_1$–$C_{12}$alkyl or phenyl, $R_7$ and $R_8$ are H, $C_1$–$C_{12}$alkyl, phenyl or $R_7$ and $R_8$, taken together, are tetramethylene, pentamethylene or 3-oxa-1,5-pentylene, $R_9$ is H or $C_1$–$C_4$alkyl, M is H or an alkali metal, $X^{\ominus}$ is the anion of a monobasic acid, and * is a stereogenic carbon atom, in the form of their racemates and diastereoisomers or mixtures of diastereoisomers. Rhodium and iridium complexes with these ligands are suitable for use as homogeneous enantioselective catalysts for the hydrogenation of prochiral compounds containing carbon double bonds or carbon/hereto atom double bonds.

6 Claims, No Drawings

FERROCENYL DIPHOSPHINES AS LIGANDS FOR HOMOGENEOUS CATALYSTS

This is a division of patent application Ser. No. 08/292,150, filed Aug. 17, 1994 now U.S. Pat. No. 5,463,097 which is a division of patent application Ser. No. 08/037,783, filed Mar. 26, 1993, now U.S. Pat. No. 5,371,256.

The present invention relates to 1-[2-(diphenylphosphino)ferrocenyl]alkylidene phosphines in the form of racemates and stereoisomers, to a process for their preparation, to iridium and rhodium complexes containing these ligands, and to the use thereof as enantioselective hydrogenation catalysts for the homogeneous hydrogenation of prochiral unsaturated compounds.

T. Hayashi et al. describe in Bull. Chem. Soc. Jpn., 53, pages 1136–1151, the preparation of a chiral ferrocenyl phosphine as ligand for transition metal complexes for asymmetric synthesis, namely [(R)-[(S)-2-(diphenylphosphino)ferrocenyl]ethyl]diphenylphosphine. Our investigations have revealed that homogeneous hydrogenations of prochiral compounds with rhodium complexes, which contain these ligands give only low optical yields.

It has now been found that, in the same or seven shorter reaction times, the enantioselectivity can be substantially enhanced if the substituents in the alkylidene phosphine group are not both phenyl.

In one of its aspects, the invention relates to compounds of formula I

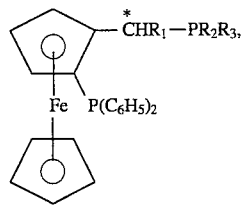

wherein $R_1$ is $C_1$–$C_8$alkyl, phenyl or phenyl which is substituted by 1 to 3 $C_1$–$C_4$alkyl or $C_1$–$C_4$alkoxy groups; $R_2$ and $R_3$ are identical and are $C_1$–$C_{12}$alkyl, $C_5$–$C_{12}$cycloalkyl or $C_1$–$C_4$alkyl- or $C_1$–$C_4$alkoxy-substituted $C_1$–$C_{12}$cycloalkyl, or phenyl which is substituted by one to three identical or different members selected from the group consisting of $C_1$–$C_4$alkyl, $C_1$–$C_4$alkoxy,—$SiR_4R_5R_6$, halogen, —$SO_3M$, —$CO_2M$,—$PO_3M$,—$NR_7R_8$ and —$[^{\oplus}NR_7R_8R_9]X^{\ominus}$; or $R_2$ and $R_3$ are different and are $C_1$–$C_{12}$alkyl, $C_5$–$C_{12}$cycloalkyl, $C_1$–$C_4$alkyl- or $C_1$–$C_4$alkoxy-substituted $C_5$–$C_{12}$cycloalkyl, phenyl or phenyl which is substituted by one to three identical or different members selected from the group consisting of $C_1$–$C_4$alkyl, $C_1$–$C_4$alkoxy,—$SiR_4R_5R_6$, halogen, —$SO_3M$, —$CO_2M$, —$PO_3M_2$, —$NR_7R_8$ and —$[^{\oplus}NR_7R_8R_9]X^{\ominus}$; or the group —$PR_2R_3$ is a radical of formula II

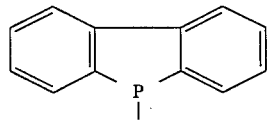

and $R_4$, $R_5$ and $R_6$ are each independently of one another $C_1$–$C_{12}$alkyl or phenyl, $R_7$ and $R_8$ are H, $C_1$–$C_{12}$alkyl, phenyl or $R_7$ and $R_8$, taken together, are tetramethylene, pentamethylene or 3-oxa-1,5-pentylene, $R_9$ is H or $C_1$–$C_4$alkyl, M is H or an alkali metal, $X^{\ominus}$ is the anion of a monobasic acid, and * is a stereogenic carbon atom, in the form of their racemates and diastereoisomers or mixtures of diastereoisomers.

$R_1$ as alkyl may be linear or branched and contains preferably 1 to 4 carbon atoms. Typical examples are methyl, ethyl, n- and isopropyl, n-, iso- and ten-butyl, pentyl, hexyl, heptyl and octyl. Methyl and ethyl are preferred and methyl is especially preferred.

$R_1$ as substituted phenyl preferably contains 1 or 2 substituents. Alkyl substituents may typically be methyl, ethyl, n- and isopropyl, n-, iso- and tert-butyl; methyl and ethyl are preferred. Alkoxy substituents may be methoxy, ethoxy, n- and isopropoxy, n-, iso- and tert-butoxy. Methoxy and ethoxy are preferred.

$R_2$ and $R_3$ as alkyl may be linear or branched and contain preferably 1 to 8, most preferably 1 to 4, carbon atoms. Typical examples are methyl, ethyl, n- and isopropyl, n-, iso- and tert-butyl, pentyl, hexyl, heptyl, octyl nonyl, decyl, undecyl and dodecyl. Methyl, ethyl, n- and isopropyl, n-, iso- and tert-butyl are preferred. When $R_2$ and $R_3$ are identical and alkyl they are most preferably isopropyl or tert-butyl.

$R_2$ and $R_3$ defined as cycloalkyl preferably contain 5 to 8, most preferably 5 or 6, ring carbon atoms. Exemplary of cycloalkyl are cyclopentyl, cyclohexyl, cycloheptyl, cyclooctyl, cyclodecyl and cycledodecyl. Cyclopentyl and cyclohexyl are preferred and cyclohexyl is especially preferred.

Cycloalkyl may be substituted, conveniently by 1 to 3 alkyl or alkoxy groups. Examples of such groups have been indicated above. Methyl and ethyl are preferred, as are also methoxy and ethoxy. Substituted cycloalkyl is typically methyl- and methoxycyclopentyl and methyl- and methoxycyclohexyl.

$R_2$ and $R_3$ defined as substituted phenyl preferably contains 1 or 2 substituents. Where phenyl contains 2 or 3 substituents, these may be identical or different.

Examples of alkyl and alkoxy substituents have been indicated above. Preferred alkyl and alkoxy substituents of phenyl are methyl, ethyl as well as methoxy and ethoxy.

Halogen as a substituent of phenyl may preferably be selected from the group consisting of —F, —Cl and —Br.

$R_4$, $R_5$ and $R_6$ may be linear or branched alkyl that preferably contains I to 8 and, most preferably, 1 to 4, carbon atoms. Exemplary alkyl substituents have been indicated above. Preferably alkyl is methyl, ethyl, n-propyl, n-butyl and tert-butyl. The substituent —$SiR_4R_5R_6$ is most preferably trimethylsilyl.

Among the acid phenyl substituents —$SO_3M$, —$CO_2M$ and —$PO_3M$, the —$SO_3M$ group is preferred. M is preferably H, Li, Na and K.

$R_7$ and $R_8$ as alkyl preferably contain 1 to 6, most preferably 1 to 4, carbon atoms. Alkyl is preferably linear. Preferred examples are methyl, ethyl, n-propyl and n-butyl. $R_9$ as alkyl is preferably methyl.

$X^{\ominus}$ as anion of a monobasic acid is preferably $Cl^{\ominus}$, $Br^{\ominus}$ or the anion of a carboxylic acid, typically formate, acetate, trichloroacetate or trifluoroacetate.

Representative examples of substituted phenyl are 2-methylphen-1-yl, 3-methylphen-1-yl, 4-methylphen-1-yl, 2- or 4-ethylphen-1-yl, 2- or 4-isopropylphen-1-yl, 2- or 4-tert-butylphen-1-yl, 2-methoxyphen-1-yl, 3-methoxyphen-1-yl, 4-methoxyphen-1-yl, 2- or 4-ethoxyphen-1-yl, 4-trimethylsilylphen-1-yl, 2- or 4-fluorophen-1-yl, 2,4-difluorophen-1-yl, 2- or 4-chlorophen-1-yl, 2,4-dichlorophen-1-yl, 2,4-dimethylphen-1-yl, 3,5-dimethyl-phen-1-yl, 2-methoxy-4-methylphen-1-yl, 3,5-dimethyl-4-methoxyphen-1-yl, 3,5-dimethyl-4-(dimethylamino)phen-1-yl, 2- or 4-aminophen-1-yl, 2- or 4-methylaminophen-1-yl, 2- or 4-(dimethylamnio)phen-1-yl, 2- or 4-$SO_3H$-phen-1-yl, 2- or 4-SO₃Na-phen-1-yl, 2-or 4—[⊕NH₃Cl⊖]phen-1-yl, 3,4,5-trimethylphen-1-yl or 2,4,6-trimethylphen-1-yl.

$R_2$ and $R_3$ as identical substituents are preferably cyclohexyl, 2- or 4-methylphen-1-yl, 2- or 4-methoxyphen-1-yl, 2- or 4-(dimethylamino)phen-1-yl, 3,5-dimethyl- 4-(dimethyl-amino)phen-1-yl and 3,5-dimethyl-4-methoxyphen-1-yl.

Where $R_2$ and $R_3$ are different substituents, $R_2$ is preferably phenyl and $R_3$ is preferably cyclohexyl, 2- or 4-methylphen-1-yl, 2- or 4-methoxyphen-1-yl, 4-(dimethylamino)-phen-1-yl, 3,5-dimethyl-4-(dimethylamino)phen-1-yl, 3,5-dimethyl-4-methoxyphen-1-yl or 4-tert-butyl-phen-1-yl.

In a preferred embodiment of the invention, $R_2$ and $R_3$ are identical substituents and are cyclohexyl.

In another preferred embodiment of the invention, $R_2$ and $R_3$ are identical substituents and are ten-butyl or o-anisyl.

In yet a further preferred embodiment of the invention, $R_2$ is phenyl and $R_3$ is o-anisyl.

In a particularly preferred preferred embodiment of the invention, $R_1$ in formula I is methyl and $R_2$ and $R_3$ are each cyclohexyl.

In another of its aspects, the invention provides a process for the preparation of compounds of formula I, which comprises teaching a compound of formula III

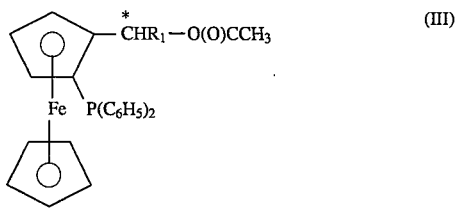

in the presence of an inert solvent at room temperature or at elevated temperature, with a phosphine of formula IV $$HPR_2R_3 \qquad (IV).$$

The reaction is known per se and is described by T. Hayashi et al. im Bull. Chem. Soc. Jpn., 53, pp. 1136–1151. The preparation of compounds of formula IIi is also described in this reference or can be carded out in analogous manner. The phosphines of formula IV are known or are obtainable by known methods in analogous manner.

The reaction temperature may be in the range from 20° to 150° C., preferably from 40° to 100° C. Suitable solvents are polar protic and aprotic solvents which may be used singly or as mixtures of two or more solvents. Typical examples of solvents are alkanols such as methanol and ethanol, and carboxylic acids such as formic acid and acetic acid, The compounds of formula I are obtained as racemates, mixtures of stereoisomers or as stereoisomers, depending on whether the compounds of formula III are used as racemates, mixtures of stereoisomers or as stereoisomers. Mixtures of stereoisomers can be separated by known methods into the stereoisomers, preferably as a rule by chromatographic methods.

The compounds of formula I are isolated and purified by per se known methods, typically by distillation, extraction, crystallisation and/or chromatographic methods.

The compounds of formula I are suitable for use as ligands for rhodium and iridium complexes. In another of its aspects, the invention relates to complexes of formulae V and VI, $$[X_1M_1YZ] \qquad (V),$$

$$[X_1M_1Y]^\oplus A_1^\ominus \qquad (VI),$$

wherein $X_1$ is two $C_2$–$C_{12}$olefins or a $C_5$–$C_{12}$diene, Z is Cl, Br or I, $A_1^\ominus$ is the anion of an oxyacid or complex acid, $M_1$ is Rh or Ir, and Y is a diphosphine of formula I. The complexes of formula VI are preferred.

With respect to the diphosphines of formula I, the same preferences and exemplifications apply as stated previously. $X_1$ as olefin preferably contains 2 to 6 and, most preferably, 2 to 4, carbon atoms. Ethylene is particularly preferred. Further examples are propene and 1-butene. $X_1$ as diene preferably contains 5 to 8 carbon atoms. The diene may be an open-chain or mono- or bicyclic diene. The two olefinic groups of the diene are preferably linked through one or two $CH_2$ groups. Typical examples are 1,3-pentadiene, cyclopentadiene, 1,5-hexadiene, 1,4-cyclohexadiene, 1,4-or 1,5-heptadiene, 1,4-or 1,5-cycloheptadiene, 1,4- or 1,5-octadiene, 1,4- or 1,5-cyclooctadiene, norbornadiene. $X_1$ is preferably two ethylene, 1,5-hexadiene, 1,5-cyclooctadiene or norbornadiene.

Z in formula V is preferably Cl or Br. Typical examples of $A_1^\ominus$ in formula VI are $ClO_4^\ominus$, $FSO_3^\ominus$, $CH_3SO_3^\ominus$, $CF_3SO_3^\ominus$, $BF_4^\ominus$, $PF_6^\ominus$, $SbCl_6^\ominus$, $AsF_6^\ominus$ and $SbF_6^\ominus$. Preferably $A_1$ is $^\ominus ClO_4^\ominus$, $CF_3SO_3^\ominus$, $BF_4^\ominus$, $PF_6^\ominus$ and $SbF_6^\ominus$.

The novel complexes are obtained in per se known manner by the reaction of equimolar amounts of a compound of formula I with a metal complex of formula $[M_1(X_1)Z]_2$ or $M_1(X_1)_2^\oplus A_1^\ominus$, wherein $M_1$, $X_1$, Z and $A_1^\ominus$ have the meanings previously assigned to them. The metal complexes are known, q.v. inter alia EP-A-0 302 021 and U.S. Pat. No. 5,011,995.

The reaction is conveniently carried out under an inert gas atmosphere, typically argon, and expediently in the temperature range from 0° to 40° C., preferably at room temperature. The concurrent use of a solvent or mixture of solvents is advantageous, conveniently selected from the group consisting of hydrocarbons (benzene, toluene, xylene), halogenated hydrocarbons (methylene chloride, chloroform, chlorobenzene), alkanols (methanol, ethanol, ethylene glycol monomethyl ether), and ethers (diethyl ether, dibutyl ether, ethylene glycol .dimethyl ether, tetrahydrofuran, dioxane) or mixes thereof. The novel complexes can be isolated and purified by conventional methods, or they can be prepared in situ prior to hydrogenation and then used in dissolved form direct as hydrogenation catalyst.

The novel complexes are preeminently suitable for use as homogeneous catalysts for the enantioselective hydrogenation of prochiral compounds containing carbon double bonds and carbon/hetero atom double bonds, typically compounds that contain a group selected from C=C, C=N, C=O, C=C—N and C=C—O [q.v. inter alia K. E. K önig. The Applicability of Asymmetric Homogeneous Catalysis, in James D. Morrison (ed.), Asymmetric Synthesis, Vol. 5, Academic Press, 1985]. Examples of such compounds are prochiral olefins, enamines, imines and ketones. Surprisingly high yields are obtained, normally even a quantitative chemical conversion, in short reaction times. Particularly surprising are the very high optical yields which are obtained with the novel complexes. The enantiomer excess (ee) may be more than 90%. It is possible to use racemates, mixtures of stereoisomers or stereoisomers of the complexes of formulae V and VI, mixtures of stereoisomers or stereoisomers being preferred.

In another of its aspects, the invention relates to the use of the novel complexes of formulae V and VI as homogeneous catalysts for the asymmetric hydrogenation of prochiral compounds containing carbon double bonds or carbon/hetero atom double bonds, especially those containing a C=C, C=N, C=O, C=C—N or C=C—O group. The preferred utility is for hydrogenating unsymmetric carbon double bonds, ketimines and ketones. The iridium complex of formulae V and VI is also preferred as catalyst for hydrogenating prochiral N-arylketimines to optically active second amines. The rhodium complex of formulae V and VI is preferably used as catalyst for hydrogenating carbon double bonds, for example prochiral carbon double bonds.

In yet another of its aspects, the invention provides a process for the asymmetric hydrogenation of prochiral compounds containing carbon double bonds or carbon/hetero atom double bonds under homogeneous reaction conditions, which process comprises hydrogenating said compounds in the temperature range from −20° to +80° C., and under a hydrogen pressure of $10^4$ to $10^7$ Pa, in the presence of a catalytic amount of a complex of formula V or VI.

Preferred prochiral compounds are those previously mentioned. Unsymmetric ketimines and ketones are known. Suitable N-arylketimines are disclosed, inter alia, in EP-A-0 256 982. N-Aliphatic ketimines are disclosed, inter alia, in EP-A-O 301 457. Such imines can be prepared from the corresponding unsymmetric ketones, which are known and commercially available or obtainable by known methods. Suitable substituted alkenes are described in the publication of K. E. König referred to above.

The process is preferably carried out in the temperature range from −10° to 50° C. and preferably under a hydrogen pressure of $1–10^5$ to $6–10^6$ Pa.

The amount of catalyst is preferably chosen such that the molar ratio of compound to be hydrogenated (substrate) to the complex of formula V or VI is preferably 10 000 to 20, more preferably 5000 to 20, especially 2000 to 40 and, most preferably, 1000 to 50.

A preferred mode of carrying out the process comprises the additional concurrent use of an ammonium or alkali metal chloride, bromide or iodide, especially when using the novel iridium catalysts. The amount may typically be 0.1 to 100, preferably 1 to 50 and, most preferably, 2 to 20, equivalents, based on the complex of formula V or VI. The addition of iodides is preferred. Ammonium is preferably tetralkylammonium containing 1 to 6 carbon atoms in the alkyl groups, and the preferred alkali metal is lithium, sodium and potassium.

The hydrogenation can be carried out without, or in the presence of, a solvent. Suitable solvents, which may be used alone or in admixture, are typically: aliphatic and aromatic hydrocarbons (pentane, hexane, cyclohexane, methylcyclohexane, benzene, toluene, xylene), alcohols such as methanol, ethanol, propanol and butanol; ethers such as diethyl ether, diethylene glycol dimethyl ether, ethylene glycol dimethyl ether, tetrahydrofuran and dioxane; halogenated hydrocarbons such as methylene chloride, chloroform, 1,1,2,2-tetrachloroethane and chlorobenzene; esters and lactones such as ethyl acetate, butyrolactone or valerolactone; carboxamides and lactams such as dimethyl formamide, dimethyl acetamide and N-methylpyrrolidone. Preferred mixes are those of alcohols and aromatic hydrocarbons, typically methanol/benzene or methanol/toluene. The preferred solvent is methanol by itself or in admixture with benzene or toluene.

The novel hydrogenation process makes it possible to obtain optically pure compounds which are useful intermediates for the synthesis of biologically active compounds, especially in the pharmaceutical and agrochemical sectors. Thus, for example, herbicidally active 5-imidazolecarboxylic acid derivatives which can be used for weed control (EP-A-0 207 563) can be prepared from secondary amines, especially N-carbalkoxymethylamines. The optically pure α-aminocarboxylates are suitable for peptide syntheses. Optically pure aminocarboxylic acids which are useful synthesis components can be obtained from unsaturated aminocarboxylic acids.

The following Examples illustrate the invention in more detail. The reactions are carried out under argon. The chemical conversion is determined by gas chromatography [column DB 17/30 W (15 m), supplier: JCW Scientific INC., USA, temperature program: 60/1 min up to 220° C., ΔT: $10°\cdot\text{min}^{-1}$]. The determination of the optical yield, enantiomer excess ee) is likewise made by gas chromatography [column Chirasil-Val, 50 m, supplier. Alltech, USA, T: 150° C., isotherm).

A) WORKING EXAMPLES

Example A1:
{(R)-1-[(S)-2-(diphenylphosphino)ferrocenyl]}ethyl dicyclohexylphosphine (A).

3.88 g (8.5 mmol) of {[(R)-1-[(S)-2-(diphenylphosphino)ferrocenyl]}ethyl acetate ([(R)-(S)-PPFOAc), prepared in accordance with Bull. Chem. Soc. Jpn., 53, 1138 (1980)], 60 ml of acetic acid and 1.9 ml (9.35 mmol) of dicyclohexylphosphine are charged in succession to a 25 ml Schlenk flask under argon and then heated, with stirring, for 2.5 hours to 50° C. To the cooled reaction solution are then added 100 ml of diethyl ether. The ether phase is separated and extracted repeatedly in succession with aqueous sodium chloride solution (saturated) and aqueous sodium hydrogencarbonate solution. The combined aqueous phases are extracted once more with diethyl ether. The ether phases are dried and concentrated. Purification by chromatography over basic alumina (solvent: hexane/ethyl acetate 9:1) followed by recrystallisation of the crude product from hot ethanol gives 42 g of A (yield: 81%) as an orange crystalline substance. $[\alpha]_D^{20}$:−349(c =1.025, CHCl$_3$); melting point: 95°−100° C.; $^{31}$P-NMR (CDCl$_3$): 15.7 (d, J=30), −25.8 (d,J=30).

Example A2:
{(R)-1-[(S)-2-diphenylphosphino)ferrocenyl]}ethyl bis(2-methoxyphenyl)phosphine (B).

The general procedure described in Example A1 is repeated, but using 0.42 g (1.68 mmol) of bis(2-methoxyphenyl)phosphine. The yield is 496 mg of B (46%) as an orange crystalline substance. $^{31}$P-NMR (CDCl$_3$): −21.6 (d, J=11),−25.3 (d, J=11).

Example A3:
{(R*$_p$)-(R)-1-[(S)-2-diphenylphosphino)ferrocenyl]}- ethylphenyl-(2-methoxyphenyl)phosphine (C).

The general procedure described in Example A1 is repeated, but using 0.36 g (1.68 mmol) of phenyl-(2-methoxyphenyl)phosphine. The yield is 555 mg of C (54%) as an orange crystalline substance. $^{31}$P-NMR (CDCl$_3$): −6.1 (d, J=16), −25.5 (d, J=16) (1st stereoisomer); −7.9 (d, J=14), −25.1 (d, J=14) (2nd stereoisomer).

Example A4;
[Norbornadiene-{(R)-1-[(S)-2-diphenylphosphino)- ferrocenyl]}ethyl-dicyclohexylphosphinorhodium tetrafluoroborate](D).

In a 25 ml Schlenk flask, 100 mg (0.267 mmol) of bis(norbornadiene)rhodium tetrafluoroborate are dissolved, under argon, in 10 ml of a mixture of methanol/methylene chloride (1:1) and then 159 mg (0.267 mmol) of A are added. This reaction is stirred for 60 minutes at room temperature and the solvent is subsequently removed under a high vacuum. The crude product is dissolved in 4 ml of methylene chloride. Precipitation with 15 ml of diethyl ether gives 192 mg of an orange crystalline substance (D) (82%). $^{31}$P-NMR (CDCl$_3$): 23.1 ($J_{RhP}$=153, $J_{pp}$=36), 52.6 ($J_{RhP}$=154, $J_{pp}$=36).

Example A5:
{(R)-1-[(S)-2-(diphenylphosphino)ferrocenyl]}ethyl-di-tert-butylphosphine (E)

The general procedure described in Example A1 is repeated, but using 1 g of (R)-(S)-PPFOAc (2.2 mmol) and 0.37 g of di-tert-butylphosphine (2.5 mmol). The yield is 704 mg of E (59%) as an orange crystalline substance. $^{31}$P-NMR (CDCl$_3$): 49.9 (d, J=50), −26.1 (d, J=50).

Example A6:
{(R)-1-[(S)-2-(diphenylphosphino)ferrocenyl]}ethyl-bis(2,4,6-trimethylphenyl)phosphine (F).

The general procedure described in Example A1 is repeated, but using 0.5 g of (R)-(S)-PPFOAc (1.1 mmol) and 0.37 g of bis(2,4,6-trimethylphenyl)phosphine (13.3 mmol). The yield is 313 mg of E (47%) as an orange crystalline substance. $^{31}$P-NMR (CDCl$_3$): −6.8 (d, J=17), −25.0 (d, J=17).

Example A7:
[{(R)-1-[(S)-2-(diphenylphosphino)ferrocenyl]}-ethyl-bis(4-methoxyphenyl)phosphine (G).

The general procedure described in Example A1 is repeated, but using 0.548 g (1.2 mmol) of (R)-(S)-PPFOAc and 0.29 ml of bis(4-methoxyphenyl)phosphine (1.3 mmol). The yield is 0.3 g (39%) as an orange foam. $^{31}$P-NMR (CDCl$_3$): 2.5 (d, J=16), −25.5 (d, J=16).

Example A8:
{(R$_p$)-(R)-1-[(S)-2-(diphenylphosphino)ferrocenyl]}-ethyl-(2-methoxyphenyl)phenylphosphine (H).

2.793 g of the mixture of diastereoisomers C (4.6 mmol) are added to a suspension of 1.325 g of [Pd$_2$Cl$_2$((R)-(+)-C$_6$H$_4$CHCH$_3$N(CH$_3$)$_2$)$_2$] (2.3 mmol) in 25 ml of methanol. The resultant red solution is stirred at room temperature for 30 minutes and then filtered. A solution of 0.372 g of NH$_4$PF$_6$ (2.3 mmol) in 6 ml of H$_2$O is slowly added dropwise and the orange suspension is stirred for a further 16 hours. The yellow precipitate is collected by filtration and washed with 20 ml of methanol (50%) and 20 ml of Et$_2$O. (The working up of filtrate I is described in Example A9). Two recrystallisations from acetone give 1.4 g of [Pd((R)-(+)-C$_6$H$_4$CHCH$_3$N(CH$_3$)$_2$(H))] (Yield: 61%). $^{31}$P-NMR (CDCl$_3$): 57.0 (d, J=43.8), 4.7 (d, J=43,8). 1.2 g of [Pd((R)-(+)-C$_6$H$_4$CHCH$_3$N(CH$_3$)$_2$(H))] (1.19 mmol) are dissolved in a mixture of 9 ml of acetone and 0.8 ml of hydrochloric acid (10N) and the solution is stirred for 10 minutes at reflux temperature. Then 20 ml of water are added at room temperature. The orange suspension is concentrated and filtered. The orange-red solid is washed with water and dried under a high vacuum. To a suspension of this solid in 20 ml of methanol are added 3.0 g of KCN (46.1 mmol). After addition of 10 ml of water and 15 ml of dichloromethane two phases form. The organic phase is dried over MgSO$_4$ and concentrated. Chromatography of the orange powder (basic alumina, hexane/ethyl acetate=9:1) gives the free ligand H in quantitative yield. Recrystallisation from ethanol gives the pure diastereoisomer ligand in a yield of 0.589 g (81.4%). $^{31}$P-NMR (CDCl$_3$): −6.1 (d, J=16), −25.5 (d, J=16).

Example A9:
{(S$_p$)-(R)-1-[(S)-2-(diphenylphosphino)ferrocenyl]}-ethyl-(2-methoxyphenyl)phenylphosphine (J).

The general procedure described in Example A8 is repeated. The filtrate I obtained in Example A8 is reacted with a solution of 0.5 g of NH$_4$PF$_6$ (3.1 mmol) in 6 ml of water. The brownish-red precipitate is collected by filtration and washed with 20 ml of aqueous methanol (50%) and 20 ml of Et$_2$O. Two recrystallisations from acetone/Et$_2$O give 1.2 g of red crystals (yield: 52%). $^{31}$P-NMR (CDCl$_3$): 30.6 (d, J=43.5), 36.2 (d, J=43.5). 1.2 g of [Pd((R)-(+)-C$_6$H$_4$CHCH$_3$N(CH$_3$)$_2$(J)]](1.19 mmol) are reacted with KCN as described in Example A8, giving 0.617 g (yield: 85% ) of pure diastereoisomer J. $^{31}$P-NMR (CDCl$_3$): −7.9 (d, J=14), −25,1 (d, J=14).

Example A10:
{(R)-1-[(S)-2-(diphenylphosphino)ferrocenyl]}ethyl-bis(4-trifluoromethylphenyl)phosphine (K).

The general procedure described in Example A1 is repeated, but using 1.0 g of (R)-(S)-PPFOAc (2.2 mmol) and 0.82 g of bis(4-trifluoromethylphenyl)phosphine (2.55 mmol). The yield is 1.20 g of K (76%) as an orange crystalline substance. $^{31}$P-NMR (CDCl$_3$): 6.6 (d, J=24), −26.4 (d, J=24).

B) USE EXAMPLES

Example B1: Preparation of N-acetylalinine Methyl Ester

A catalyst solution (prepared under argon) consisting of 12.9 mg (0.034 mmol) of [Rh(norbomadiene)$_2$]BF$_4$, 19.0 mg (0.037 mmol) of A and 5 ml of methanol is transferred by a steel capillary to a 200 ml glass reactor under argon. A solution of 750 mg (3.42 mmol) of Z-methyl-2-acetamidocinnamate (substrate) and 5 ml of methanol are then added in analagous manner. The molar ratio of substrate/catalyst is 100. Then hydrogenation is carried out with hydrogen in three cycles under a pressure of 0. 1 MPa and the hydrogen pressure is adjusted to 0.108 MPa. The reaction mixture is stirred for 30 minutes at 25° C. and then transferred to a flask and the solvent is stripped off on a rotary evaporator. The a chemical conversion is 100%, and the N-acetylalinine methyl ester is obtained in an entiomer excess (ee) of 94% (R).

Example B2: Preparation of N-acetylalanine Methyl Ester

The general procedure described in Example B1 is repeated, with the following modifications to the reaction conditions: 24.4 mg (0.037 mmol) of B; reaction time 1 hour, hydrogen pressure 50 bar. The conversion is 100%, ee: 83% (R).

Example B3: Preparation of N-acetylalanine Methyl Ester

The general procedure described in Example B1 is repeated, with the following modifications to the reaction conditions: [Rh(norbomadiene)$_2$]BF$_4$ 8.3 mg (0.022 mmol); 15 mg (0.025 mmol) of C (ratio of the two stereoisomers 1); Z-methyl-2-acetamidocinnamate 0.49 g (2.22 mmol); reaction time 2 hours. The conversion is 100%, ee: 79% (R).

Example B4: Preparation of dimethyl-2-methylsuccinate

The general procedure described in Example B1 is repeated, with the following modifications to the reaction conditions: [Rh(norbornadiene)$_2$]BF$_4$ 11.8 mg (0.032 mmol); 20.7 mg (0.035 mmol) of A; dimethyl itaconate (substrate) 0.5 g (3.2 mmol); reaction time 30 minutes. The conversion is 100%, ee >95%.

Example 5: Preparation of N-acetylalanine Methyl Ester

The general procedure described in Example B1 is repeated, with the following modifications to the reaction conditions: [Rh((norbornadiene)Cl]$_2$: 3.9 mg (0.0085 mmol); E: 10.3 mg (0.019 mmol); solvent: 11 ml of toluene/methanol (10:1); hydrogen: 15 bar, temperature: 0° C.; reaction time: 20 hours. The conversion is 100%, ee: 73.6% (R).

Example B6: Preparation of N-(2',6'-dimethylphenyl)-1-methoxymethylethylamine The general procedure described in Example B1 is repeated, with the following modifications to the reaction conditions: A catalyst solution is prepared consisting of 5.3 mg of [Ir((1,5-cyclooctadien)Cl]$_2$ (0.0079 mmol), 10.2 mg of A (0.017 mmol) and 11.9 mg of tetrabutylammonium iodide (0.032 mmol) in 5 ml of tetrahydrofuran/dichloromethane (1:1). A substrate solution consisting of 1.5 g of N-(2',6'-dimethylphenyl)-1-methoxymethyl-ethylideneamine (7.8 mmol) in 5 ml of tetrahydrofuran is also used. Hydrogenation is carried out with hydrogen under a pressure of 40 bar. The reaction temperature is 30° C. After 91 hours the conversion is 90%, the ee is 59% (R).

Example 7: Preparation of N-(2',6'-dimethylphenyl)-1-methoxymethylethylamine The general procedure described in Example B1 is repeated, with the following modifications to the reaction conditions: A catalyst solution is prepared consisting of 5.3 mg of [Ir((1,5-cyclooctadiene)Cl]$_2$ (0.0079 mmol) and 11.1 mg of G (0.017 mmol); reaction time: 20 hours. The conversion is 100%, ee: 56.6% (S).

Example B8: Preparation of Methyl-2-hydroxy-2-phenylacetate

The general procedure described in Example B1 is repeated, with the following modifications to the reaction conditions: [Rh((norbornadiene)Cl]$_2$:3.9 mg (0.0082 mmol); E: 9.7 mg (0.018 mmol); methyl phenyl glyoxylate (substrate): 0.268 mg (1.64 mmol); solvent: 10 ml of toluene; hydrogen: 40 bar;, temperature: 70° C.; reaction time: 20 hours. The conversion is 100%, ee: 41%.

Example B9: Preparation of N-acetylalanine

The general procedure described in Example B1 is repeated, with the following modifications to the reaction conditions: acetamidocinnamic acid (substrate): 0.83 g (3.43 mmol). The conversion is 100%, ee: 81% (R).

Example B10: Preparation of N-acetylalanine Methyl Ester

The general procedure described in Example B1 is repeated, with the following modifications to the reaction conditions: H: 18.3 mg (0.037 mmol). The conversion is 100%, ee: 79% (R).

Example B11: Preparation of Ethyl-4-phenyl-2-hydroxybutyrate

The general procedure described in Example B1 is repeated, with the following modifications to the reaction conditions: ethyl-4-phenyl-2-oxobutyrate (substrate): 0.352 g (1.7 mmol); solvent: 10 ml of toluene/methanol (1:1); hydrogen: 50 bar, temperature: 50° C.; reaction time: 19 hours. The conversion is 100%, ee: 44% (R).

What is claimed is:

1. A process for the asymmetric hydrogenation of compounds containing carbon double bonds or carbon/hetero atom double bonds selected from C=N, C=O, C=C—N and C=C—O groups under homogeneous reaction conditions, which comprises hydrogenating said compounds in the temperature range from −20° to +80° C. and under a hydrogen pressure of $10^4$ to $10^7$ Pa in the presence of a catalytic amount of a complex of the formula V or VI

$$[X_1M_1YZ_1] \quad \quad (V)$$

$$[X_1M_1Y]^{\oplus}A_1^{\ominus} \quad \quad (VI)$$

wherein $X_1$ is two $C_2$–$C_2$olefins or a $C_5$–$C_{12}$diene,

Z is Cl, Br or I, $A_1^{\ominus}$ is the anion of an oxyacid or a complex acid, $M_1$ is Rh or Ir, and Y is a compound of the formula I

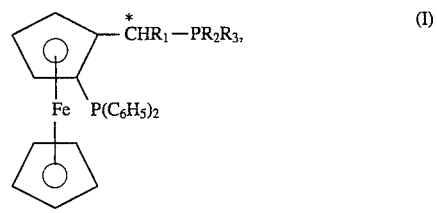

wherein $R_1$ is $C_1$–$C_8$alkyl, phenyl or phenyl which is substituted by 1 to 3 $C_1$–$C_4$alkyl or $C_1$–$C_4$alkoxy groups; $R_2$ and $R_3$ are identical and are $C_1$–$C_{12}$alkyl, $C_5$–$C_{12}$cycloalkyl or $C_1$–$C_4$alkyl- or $C_1$–$C_4$alkoxy-substituted $C_5$–$C_{12}$cycloalkyl, or phenyl which is substituted by 4-trifluoromethyl or by one to three identical or different members selected from the group consisting of $C_1$–$C_4$alkyl, $C_1$–$C_4$alkoxy, —$SiR_4R_5R_6$, —halogen, —$SO_3M$, —$CO_2M$, —$PO_3M$, —$NR_7R_8$ and —[$^{\oplus}NR_7R_8R_9$]$X^{\ominus}$; $R_2$ and $R_3$ are different and are $C_1$–$C_{12}$alkyl, $C_5$–$C_{12}$cycloalkyl, $C_1$–$C_4$alkyl- or $C_1$–$C_4$alkoxy-substituted $C_5$–$C_{12}$cycloalkyl, phenyl or phenyl which is substituted by one to three identical or different members selected from the group consisting of $C_1$–$C_4$alkyl, $C_1$–$C_4$alkoxy, —$SiR_4R_5R_6$, halogen, —$SO_3M$, —$CO_2M$, —$PO_3M_2$, —$NR_7R_8$ and —[$^{\oplus}NR_7R_8R_9$]$X^{\ominus}$; or the group —$PR_2R_3$ is a radical of the formula II

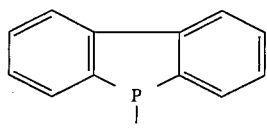

and $R_4$, $R_5$ and $R_6$ are each independently of one another $C_1$–$C_{12}$ alkyl or phenyl, $R_7$ and $R_8$ H, $C_1$–$C_{12}$alkyl, phenyl or $R_7$ and $R_8$, taken together, are tetramethylene, pentamethylene or 3-oxa-1,5-pentylene, $R_9$ is H or $C_1$–$C_4$alkyl, M is H or an alkali metal, $X^\ominus$ is the anion of a monobasic acid, and * is a stereogenic carbon atom, in the form of the racemate or diastereoisomer or mixture of diastereoisomers.

2. A process according to claim 1, wherein the hydrogen pressure is from $10^5$ to $6$–$10^6$ Pa.

3. A process according to claim 1, wherein the temperature is in the range from $-10°$ to $+50°$ C.

4. A process according to claim 1, wherein the amount of catalyst is chosen such that the molar ratio of compound to be hydrogenated (substrate) to complex of formula V or VI is 10,000 to 20.

5. A process according to claim 1, wherein the reaction is carried out in the presence of a solvent.

6. A process according to claim 1, wherein the solvent is methanol or a mixture of methanol and benzene or toluene.

* * * * *